United States Patent [19]

Kompelien

[11] 4,431,962
[45] Feb. 14, 1984

[54] CAPACITOR MONITORING BY SINGLE RESISTOR ADJUSTMENT

[75] Inventor: Arlon D. Kompelien, Richfield, Minn.

[73] Assignee: Honeywell, Inc., Minneapolis, Minn.

[21] Appl. No.: 357,235

[22] Filed: Mar. 11, 1982

[51] Int. Cl.³ .................... G01R 11/52; G01R 27/26
[52] U.S. Cl. .......................... 324/60 C; 324/DIG. 1; 324/61 R
[58] Field of Search ........... 324/60 R, 60 C, DIG. 1, 324/61 R

[56] References Cited

U.S. PATENT DOCUMENTS 3,083,565 4/1963 Jennings et al. .
3,177,427 4/1965 Kuntz et al. .
3,221,247 11/1965 Samuelian .................... 324/60 R
3,350,941 11/1967 Misevich et al. .
3,802,268 4/1974 Thoma .
4,282,480 8/1981 Fujito et al. .

Primary Examiner—Stanley T. Krawczewicz
Assistant Examiner—Jose M. Solis
Attorney, Agent, or Firm—Alfred N. Feldman

[57] ABSTRACT

A humidity element circuit calibration arrangement utilizing a humidity responsive capacitive element is provided for. A single signal generator arrangement provides two opposite phases of the same voltage to energize the circuit thereby allowing for simple calibration by the adjustment of a single resistance element.

9 Claims, 1 Drawing Figure

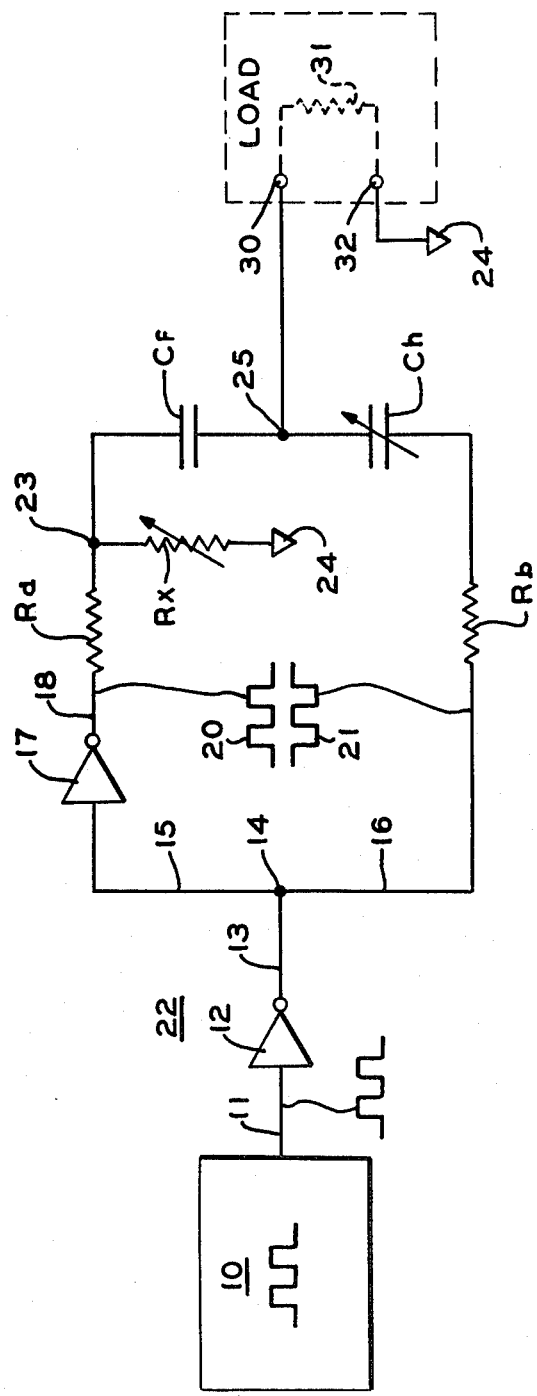

CAPACITOR MONITORING BY SINGLE RESISTOR ADJUSTMENT

BACKGROUND OF THE INVENTION

In capacitor monitoring or measuring types of circuits it has been common to use capacitor bridges typically having four legs. A four-legged type of bridge normally is fed with power across two legs and an output is differentially measured across the other two legs. In this type of a bridge, particularly one that utilizes capacitive elements in the bridge circuit, the nulling of the bridge or the measuring of a capacitive element causes an interaction which in turn normally requires trimming or adjustment of more than one element.

SUMMARY OF THE INVENTION

The present invention is directed to a simple sensing circuit which has a single output relative to ground rather than the usual outputs from a four-legged type of bridge. The present invention has particular utility in condition responsive type systems in which a capacitive element is condition responsive, such as responsive to humidity. The humidity sensitive element is a capacitor, such as a polymide dielectric type of sensor that changes capacity with humidity. This type of capacitance sensing element has a very low dissipation factor. This means that the capacitor appears to be a pure capacitor with a negligible amount of resistance. This being the case, a balance is possible with a trim adjustment on a single element. This is opposed to the normal approach of trimming or balancing the capacitor elements in the circuit. The present invention is directed to the adjustment of a single resistive element in the circuit. The resistive element is much easier to automatically adjust than would be a capacitive type element. It also allows the bridge to be balanced independent of the applied frequency, permitting a square wave drive which is easily obtained.

BRIEF DESCRIPTION OF THE DRAWING

The sole FIGURE is a circuit of a simple humidity control circuit.

DESCRIPTION OF THE PREFERRED EMBODIMENT

A signal generator means 10 is provided that is shown as a square wave generator. The square wave generator is shown for simplicity sake in considering the present invention. The output of the voltage generator means 10 is provided on a conductor 11 to a NOT gate 12 where the square wave in turn is inverted and supplied to a conductor 13. The conductor 13 separates at 14 into two voltage paths at conductors 15 and 16. The conductor 15 is connected through a NOT gate 17 to a conductor 18. The conductors 16 and 18 provide two varying voltages that are opposite phases of a single wave form as disclosed at the wave form 20 and 21. This provides an output circuit means for the voltage driving means generally disclosed at 22 which includes the voltage generator 10 and the circuitry to the output conductors 16 and 18.

The output conductor 18 is connected to a resistor Ra, while the conductor 16 is connected to a resistor Rb. For reasons that will become apparent later on, the resistors Ra and Rb are of the same magnitude. The resistor Ra is connecte at 23 to a variable resistor Rx. The variable resistor Rx is connected to ground at 24 and can be any type of variable resistance element ranging from a potentiometer to a resistor that is trimmed in a hydrid circuit application.

The junction 23 is further connected through a capacitor Cf which is a fixed capacitor having a very low dissipation factor thereby appearing as substantially a pure capacitance with negligible resistance. The capacitor Cf in turn is connected at a common point 25 to a second capacitor Ch which has been shown as a variable capacitor. The capacitor Ch is variable in nature and generally is a condition responsive capacitor, such as a humidity responsive polymide type of capacitor. The capacitor Ch could be any type of variable capacitor that varies in response to a condition (other than humidity) or could be manually adjusted, if called for by the circuit application. The capacitor Ch in turn is connected to the resistor Rb.

The common junction 25 forms a processing circuit output means for the circuit disclosed, and it is connected at terminal 30 to a load that is shown at 31 as a resistance type of load connected to a further terminal 32 which in turn is connected to ground 24. The adjustable reisistance Rx is adjusted in such a manner as to be capable of nulling the voltage at the processing circuit output means 25.

For a low cost circuit, it is easiest to drive the bridge elements from signal outputs that are being driven to saturation by potential values near the power supply values supplied by the signal generator means 10. With a regulated power supply, the output to the bridge elements, Ra, Rb, Cf, and Ch are then essentially regulated. In order for a single output to null relative to ground, the two legs must be driven with opposite phases of a signal, such as the square wave signal disclosed at 20 and 21. This is accomplished readily from a single voltage generating means 10 by the use of the NOT gate or inverter amplifier 17 in the tip leg of the circuit.

In order to understand how the null is obtained through the adjustment of resistor Rx, the following considerations and assumptions are made. It is assumed that capacitor Cf is a fixed, stable capacitor which is in the order of 50 percent larger than the variable capacitive element Ch. In this particular case the element Ch is a humidity element. If this is the case, we can define a parameter A equals Cf/Ch where A will be approximately 1.5. Now, as the voltage at 18 goes to a value of E (the power supply voltage), the value of voltage at 16 goes to 0. When this happens, the instantaneous voltage change across the resistance element Ra of the top leg must equal that of the bottom leg, since the magnitude change of the voltages at 16 and 18 are equal. For this reason, and the fact that the instantaneous current change in Ra equals Rb, resistance Rb of the bottom leg is designed equal to Ra of the top leg. This selection can reasonably be made to provide Ra sufficiently close to Rb for all practical purposes without the need for calibrations on their values. With Ra equals Rb, the instantaneous current change in Ra equals Rb at the time the driving voltage switches because the voltage cannot change instantly across the series connected capacitors Cf and Ch. Since the instantaneous change in current through Ra all flows through Cf, no instantaneous change in current occurs in Rx to add an instantaneous voltage change to Cf of the top leg. Because of this there is not an instantaneous voltage change at terminal 30 when the driving voltage switches. At null, it is also necessary that the time constant of the impedance driving capacitor Cf is equal to that of the capacitor Ch since the currents in Cf and Ch must remain equal without causing a voltage change at terminal 30. In order for these time constants to be equal, the resistor Rx must be selected. The equivalent series resistance driving capacitor Cf is Rx in parallel with Ra or RxRa/Rx+Ra. For the two time constants to be equal, RxRa/Rx+Ra times Cf must equal RbCh. Now, since Rb already equals Ra, and Cf equals (A) Ch then RxRa/Rx+Ra times ACh must equal RaCh. By substitution RxA equals Rx+Ra; or Rx equals Ra/A−1.

With this circuit then, a capacitor Cf is applied which is some factor larger than Ch, but not of a precise calibrated value. Calibration is then obtained by selecting Rx equals Ra/A−1 where A is the factor of the capacitor Cf relative to the capacitor Ch at the point we desire null. The resistor Rx can be determined by observing the output between the capacitor Cf and Ch at point 25 in the circuit while the adjustment is being made.

The present circuit can be used by measuring or amplifying the off null output voltage at terminal 30 with respect to terminal 32 (ground 24) as humidity changes the circuit from the null condition. Or, the present circuit can be used by calibrating a potentiometer making up Rx that defines null points for the entire humidity range.

The present invention discloses a very simple circuit that is capable of being used with a capacitive sensing element in which a null can be created by the simple adjustment of a single resistive element. This arrangement highly simplifies the design of a sensing circuit and provides for a very inexpensive circuit that can be readily adapted to condition control applications. The circuit has been shown in a very simplified form and it is quite obvious that may modifications in the arrangement disclosed can be undertaken by one skilled in the art. For this reason the applicant wishes to be limited in the scope of his invention solely the scope of the appended claims.

The embodiment of the invention in which an exclusive property or right is claimed are defined as follows:

1. A capacitor monitoring circuit with resistive null calibration means, including: voltage driving means including output circuit means with said output circuit means providing two varying voltages of equal amplitude and that are opposite phases of a wave form; first measuring circuit means including a first resistance connected in series with first capacitor means between processing circuit output means and a first of said varying voltages; second measuring circuit means including a second resistance connected in series with second capacitor means between said processing circuit output means and a second of said varying voltages; said first and second resistances being generally of the same magnitude; said first and said second capacitor means being of different capacitive values with one of said capacitor means being variable in nature; said first and said second capacitor means being joined at said processing circuit output means to form said processing circuit output means with respect to a ground and said output means connected to control a load; and adjustable resistance means connected between one of said capacitor means and ground to adjust the voltage applied to the capacitor means to which said adjustable resistance means is connected to null a processing circuit output means voltage with respect to ground.

2. A capacitor monitoring circuit as described in claim 1 wherein said capacitor means that is variable in nature is a condition responsive capacitor.

3. A capacitor monitoring circuit as described in claim 2 wherein said condition responsive variable capacitor is a humidity sensitive capacitor having a very low dissipation factor.

4. A capacitor monitoring circuit as described in claim 1 wherein said two varying voltages from said voltage driving means are square waves.

5. A capacitor monitoring circuit as described in claim 4 wherein said capacitor means that is variable in nature is a condition responsive capacitor.

6. A capacitor monitoring circuit as described in claim 5 wherein said condition responsive variable capacitor is a humidity sensitive capacitor having a very low dissipation factor.

7. A capacitor monitoring circuit as described in claim 6 wherein said voltage driving means includes a single wave form generator that has two output circuits; and a NOT gate in one of said output circuits to provide said two varying voltages of opposite phases.

8. A capacitor monitoring circuit as described in claim 7 wherein said fixed capacitor means is in the order of 50 percent larger than said humidity sensitive capacitor.

9. A capacitor monitoring circuit as described in claim 8 wherein said adjustable resistance means includes a potentiometer.

* * * * *